United States Patent
Gatineau et al.

(10) Patent No.: US 8,309,174 B2
(45) Date of Patent: Nov. 13, 2012

(54) HETEROLEPTIC IRIDIUM PRECURSORS TO BE USED FOR THE DEPOSITION OF IRIDIUM-CONTAINING FILMS

(75) Inventors: Julien Gatineau, Tsuchiura (JP); Christian Dussarrat, Wilminton, DE (US)

(73) Assignees: L'Air Liquide Societe Anonyme pour l'Etude et l'Exploitation des Procedes Georges Claude, Paris (FR); American Air Liquide, Inc., Fremont, CA (US)

( * ) Notice: Subject to any disclaimer, the term of this patent is extended or adjusted under 35 U.S.C. 154(b) by 680 days.

(21) Appl. No.: 12/424,265

(22) Filed: Apr. 15, 2009

(65) Prior Publication Data

US 2009/0258144 A1    Oct. 15, 2009

Related U.S. Application Data

(60) Provisional application No. 61/045,191, filed on Apr. 15, 2008.

(51) Int. Cl.
  *C23C 16/18* (2006.01)
  *C07F 15/00* (2006.01)

(52) U.S. Cl. ........... 427/255.28; 427/248.1; 427/255.23; 556/1; 556/136

(58) Field of Classification Search ............. 427/255.28, 427/248.1, 255.23; 556/1, 136
See application file for complete search history.

(56) References Cited

U.S. PATENT DOCUMENTS

| | | | | |
|---|---|---|---|---|
| 5,130,172 | A * | 7/1992 | Hicks et al. | 427/584 |
| 5,403,620 | A | 4/1995 | Kaesz et al. | |
| 6,329,286 | B1 | 12/2001 | Vaartstra | |
| 6,884,902 | B2 * | 4/2005 | Takamori et al. | 556/136 |
| 6,900,107 | B2 * | 5/2005 | Marsh | 438/396 |
| 7,217,970 | B2 | 5/2007 | Marsh | |
| 7,265,233 | B2 | 9/2007 | Kawano et al. | |
| 2004/0215029 | A1 | 10/2004 | Takamori et al. | |
| 2008/0038465 | A1 | 2/2008 | Dussarrat et al. | |
| 2008/0107812 | A1 | 5/2008 | Dussarrat et al. | |
| 2008/0152793 | A1 | 6/2008 | Gatineau et al. | |
| 2008/0248648 | A1 | 10/2008 | Thompson et al. | |
| 2009/0028745 | A1 | 1/2009 | Gatineau et al. | |
| 2009/0029036 | A1 | 1/2009 | Dussarrat | |
| 2010/0221577 | A1 | 9/2010 | Dussarrat | |

FOREIGN PATENT DOCUMENTS

| | | |
|---|---|---|
| JP | 2001 181841 | 7/2001 |
| WO | WO 2005 017950 | 2/2005 |
| WO | WO 2008 034468 | 3/2008 |

OTHER PUBLICATIONS

Chen, Y. et al., "Deposition of iridium thin films using new Ir1 CVD precursors," Chem. Vap. Deposition 2002, 8, No. 1, pp. 17-20.
Müller, J. et al., "π-Olefin-Iridium-Komplexe, IX[1] Bis($\eta^4$-butadiene)-α-organyl-iridium-Verbindungen," Z. Naturforsch. 87b (1982) pp, 1573-1579.
Yan, X. et al., "Ne MOCVD precursor for iridium thin films deposition," Materials Letters 61 (2007), pp. 216-218.

* cited by examiner

*Primary Examiner* — Matthew Daniels
*Assistant Examiner* — Dennis Cordray
(74) *Attorney, Agent, or Firm* — Patricia E. McQueeney

(57) ABSTRACT

The present invention provides a process for the deposition of a iridium containing film on a substrate, the process comprising the steps of providing at least one substrate in a reactor; introducing into the reactor at least one iridium containing precursor having the formula:

$$XIrY_A,$$

wherein A is equal to 1 or 2 and i) when A is 1, X is a dienyl ligand and Y is a diene ligand; ii) when A is 2, a) X is a dienyl ligand and Y is selected from CO and an ethylene ligand, b) X is a ligand selected from H, alkyl, alkylamides, alkoxides, alkylsilyls, alkylsilylamides, alkylamino, and fluoroalkyl and each Y is a diene ligand, and c) X is a dienyl ligand and Y is a diene ligand; reacting the at least one iridium containing precursor in the reactor at a temperature equal to or greater than 100° C.; and depositing an iridium containing film formed from the reaction of the at least one iridium containing precursor onto the at least one substrate.

13 Claims, No Drawings

HETEROLEPTIC IRIDIUM PRECURSORS TO BE USED FOR THE DEPOSITION OF IRIDIUM-CONTAINING FILMS

This application claims the benefit of U.S. Provisional Application No. 61/045,191, filed Apr. 15, 2008, the entire contents of which are incorporated herein by reference.

FIELD OF THE INVENTION

The present invention relates to iridium precursors and methods for depositing thin films containing iridium on a substrate.

BACKGROUND

The move towards the use of new materials for chip manufacturing is necessary in order to solve the various issues generated by the continuous scaling up trend imposed on the industry. Accordingly, the expectation is that a number of different chemical elements will be introduced into the industrial semiconductor manufacturing process for many applications in the coming years. With regard to the next generation nodes, iridium is considered as one of the best candidates for the electrode capacitor for FeRAM and DRAM applications. Iridium has the required properties, such as high melting point, low resistivity, high oxidation resistance, and adequate work function, thereby making it a potential gate electrode material for CMOS transistor.

A large variety of iridium CVD precursors are available. Many of these have been studied for film deposition. Most of these iridium CVD precursors contain the ligand cyclopentadienyl (Cp). Recently, low melting point molecules were mentioned in Japanese patent JP 2001181841. Table 1 of JP 2001181841 discloses a table with the physical properties of iridium Cp type ligands.

| Molecule | Melting point (° C.) | Vapor pressure (Torr) | Decomposition (° C.) |
|---|---|---|---|
| Ir(COD)(MeCp) | 40 | 0.08 at 100° C. | X |
| Ir(COD)(EtCp) | 14 | 0.1 at 105° C. | 370 |
| Ir(1,3-CHD)(EtCp) | 15 | 0.1 at 75° C. | 300 |

Other types of cyclopentadienyl containing molecules are described in U.S. Pat. No. 6,329,286. The iridium precursors described in this patent are of the formula (MeCp)Ir(CO)$_2$, which is described as a liquid at 58° C. Surprisingly, (MeCp)Ir(CO)$_2$ is used dissolved in a solvent.

Bis(ethylene)(ethylcyclopentadienyl) iridium is described in U.S. Pat. No. 7,265,233. Bis(ethylene)(ethylcyclopentadienyl) iridium is an oil and its decomposition temperature, according to DSC measurements, is 220° C. When the ethyl group is replaced by a methyl group, the molecule is a solid.

U.S. Patent Application No. 2004/0215029 discloses precursors such as (EtCp)(1,3-cyclohexadiene) iridium, (MeCp)(1,3-cyclohexadiene) iridium, and (EtCp)(2,3-Me$_2$-1,3-butadiene) iridium. (EtCp)(1,3-cyclohexadiene) iridium is described as an orange oil which decomposes from 300° C. (DSC), whereas (MeCp)(1,3-cyclohexadiene) iridium is a solid. (EtCp)(2,3-Me$_2$-1,3-butadiene) iridium is an orange oil that decomposes from 310° C.

Other precursors are also available, such as β-diketonate type precursors among which are Ir(acac)$_3$ and Ir(tmhd)$_3$. ("New MOCVD precursor for Iridium thin film deposition", X. Yan, Q. Zhang, X. Fan, Materials Letters 61 (2007), pp. 216-218). These precursors usually exhibit a very high melting point and are not adequate for metallic depositions. Basing their research on the improvement of the β-diketonate type molecules, some researchers developed heteroleptic molecules of the type (keim)Ir(COD), (hfda)Ir(COD), and (amak)Ir(COD) ("Deposition of Iridium Thin Films Using New IrI CVD Precursor", Y. Chi et al, CVD, 2002, 8(1), pp. 17-20). Such molecules have a lower melting point than homoleptic β-diketonate type molecules, 117° C., 111° C., and 127° C., respectively. Such a decrease in melting point, as well as the increase of volatility, is obtained thanks to the introduction of fluoromethyl instead of methyl.

Prior art precursors present a variety of different issues with regard to their integration into the semi-conductor industry. For example, precursors such as the β-diketonate type, have very high melting points; 270° C. for Ir(acac)$_3$ and 235° C. for Ir(tmhd)$_3$. For this reason, all of the delivery parts of the deposition tool upstream of the deposition chamber, as well as the delivery parts downstream, have to be heated to avoid absorption of the precursor onto the surface of the tube. As a result, the burden on the thermal budget becomes very important. In addition, these heated parts generate safety, as well as handling, issues. The deposition rate using these complexes is typically very low, thereby increasing a burden on the deposition process. Such precursors usually exhibit a very long incubation time.

On the other hand, some of the Cp type precursors allow for appreciable results compared to the β-diketonate type. Some of these precursors are liquid, which is an improvement with regard to the delivery of the precursor. However, the reactivity of the molecules on the substrate is still too low which results in bad nucleation of the iridium films on the substrates.

The precursors developed and set forth by Chi et al in Deposition of Iridium Thin Films Using New IrI CVD precursors, while representing an improvement of the β-diketonate type precursors, still present issues from the view point of their bad thermal stability and the incorporation of fluor elements that may be a source of impurity for the film or the sub-layers. Y. Chi et al, CVD, 2002 8 (1), pp. 17-20.

Accordingly, there is a need for a new type of iridium precursor which is stable and has a melting point below 25° C., preferably below 0° C.

SUMMARY

The present invention concerns the deposition of iridium containing films on one or more substrates by using at least one heteroleptic iridium precursor containing ligands that preferably have a higher reactivity than the prior art ligands. This iridium precursor is liquid at 25° C. and preferably liquid even below 0° C. The new iridium precursors exhibit a relatively high vapor pressure, are thermally stable at the temperature of storage and distribution, and allow deposition of iridium containing films at low temperatures. As reactivity is enhanced, films are deposited with a higher deposition rate, and with low or negligible incubation time, regardless of the type of substrate. The iridium containing film depositions with these precursors can be carried out by thermal and/or plasma-enhanced CVD, ALD, and pulse CVD.

DETAILED DESCRIPTION OF THE PRESENT INVENTION

It has now been found that by replacing at least one of the ligands of the prior art precursors with a more reactive ligand, it is possible to obtain an iridium precursor that has a melting point below 25° C., ideally below 0° C. For example, when cyclohexadienyl is substituted for cyclopentadienyl, this more reactive ligand has the characteristic of being a closed ring of carbon atoms with an open electronic cloud (whereas Cp has a closed electronic cloud). When 1-methyl-1,4-cyclohexadiene is substituted for 1,3-cyclohexadiene, this more reactive ligand increases the potential degree of asymmetry of the ligand and as such lowers the melting point of the iridium molecule.

The iridium precursors of the present invention have a relatively high thermal stability thereby preventing decomposition during the delivery of the molecule. These iridium precursors also have a relatively high vapor pressure which eases the delivery of vapors of the precursor to the reaction furnace.

As noted, the iridium precursors of the present invention are liquid at about 25° C. and preferably are liquid at temperatures around 0° C. or below. One of the main advantages of the presently claimed iridium precursors is that they can be provided as pure liquids, without the addition of a solvent. Accordingly, this enables the deposition of pure iridium films or iridium containing films depending on the co-reactant used with the precursor. As a result, the obtained films are preferably able to be deposited without a detectable incubation time. Also, with regard to the use of the present iridium precursors, an Atomic Layer Deposition (ALD) regime can preferably be obtained for pure iridium deposition as well as for deposition of other iridium containing films (for example, $IrO_2$ or Ir/Pt alloy).

Accordingly, there is provided a process for the deposition of an iridium containing film on one or more substrates. With regard to this process, the first step of the process involves providing at least one substrate into a reaction chamber of a reactor. The reactor may be any enclosure or chamber of a device in which deposition methods take place, such as, without limitation, a cold-wall type reactor, a hot-wall type reactor, a single-wafer reactor, a multi-wafer reactor, or other such types of deposition systems.

The type of substrate upon which the precursor will be deposited will vary depending on the final use intended. In some embodiments, the substrate may be chosen from oxides which are used as dielectric materials in MIM, DRAM, FeRam technologies or gate die/lectrics in CMOS technologies (for example, HfO based materials, $TiO_2$ based materials, $ZrO_2$ based materials, rare earth oxide based materials, ternary oxide based materials, etc.) or from nitride-based films (for example, TaN) that are used as an oxygen barrier between copper and the low-k layer. Other examples of substrates which can be coated using the process of the present invention include, but are not limited to, solid substrates such as metal substrates (for example, Ru, Al, Ni, Ti, Co, Pt and metal silicides, such as $TiSi_2$, $CoSi_2$, and $NiSi_2$); metal nitride containing substrates (for example, TaN, TiN, WN, TaCN, TiCN, TaSiN, and TiSiN); semiconductor materials (for example, Si, SiGe, GaAs, InP, diamond, GaN, and SiC); insulators (for example, $SiO_2$, $Si_3N_4$, $HfO_2$, $Ta_2O_5$, $ZrO_2$, $TiO_2$, $Al_2O_3$, and barium strontium titanate); or other substrates that include any number of combinations of these materials. The actual substrate utilized will also depend upon the specific precursor embodiment utilized. In many instances though, the preferred substrate utilized will be selected from TiN, Ru and Si type substrates.

After the one or more substrates are placed in the reactor, the next step of the process involves introducing into the reactor at least one iridium containing precursor of the formula (I):

$$XIrY_A \qquad (I)$$

With regard to this formula (I), A is equal to 1 or 2. In the first embodiment, A is equal to 1 (there is one Y group), X is selected from dienyl ligands and Y is selected from diene ligands. The dienyl ligands from which X is chosen include cyclopentadienyl (Cp), pentadienyl (Op), cyclohexadienyl (chdl), hexadienyl, oxocyclohexadienyl, cycloheptadienyl, heptadienyl, cyclooctadienyl, and octadienyl. Each of these dienyl ligands can optionally be substituted with an unlimited number of substituents R1, each R1 being independently selected from H, O, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides and $C_1$ to $C_4$ linear or branched fluoroalkyl. As used throughout with regard to each of the embodiments herein, the phrase "an unlimited number of substituents" refers not to an indefinite number of substitutions but instead refers to a limited number of substitutions, this limited number of substitutions being determined based on the actual ligand (and resulting available sites for substitution) utilized. However, with regard to this particular embodiment wherein A is 1, when X is a substituted pentadienyl, a substituted cyclopentadienyl, or a substituted cycloheptadienyl, the X substituents will not be fully substituted; they will lack at least one substitution to qualify as full substitution thereby leaving at least one available site for substitution.

In the present embodiment, X is preferably selected from cyclopentadienyl (Cp) and cyclohexadienyl (chdl), even more preferably cyclopentadienyl (Cp) and cyclohexadienyl (chdl) that are each independently substituted with one or more substituents R1, each R1 being independently selected from methyl ($CH_3$), ethyl ($C_2H_5$), propyl ($C_3H_7$) and mixtures thereof. In the most preferred embodiment where A is 1, X is either substituted cyclopentadienyl (Cp) or substituted cyclohexadienyl (chdl), each being substituted with from 1 to 7 R1 groups, preferably from 1 to 5 R1 groups, with each R1 group being independently selected from methyl ($CH_3$) and ethyl ($C_2H_5$). With regard to this most preferred embodiment, as noted above, in the case where X is cyclopentadienyl, the substitution will not be a full substitution.

In this embodiment where A is 1, Y is a diene ligand that is selected from butadiene, cyclopentadiene, pentadiene, hexadiene, 1,3-cyclohexadiene, 1,4-cyclohexadiene, and oxocyclohexadiene. Each of these diene ligands can optionally be substituted by an unlimited number of substituents R2, each R2 being independently selected from H, O, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides, and $C_1$ to $C_4$ linear or branched fluoroalkyl. Preferably, in this particular embodiment, Y is selected from 1,3-cyclohexadiene, 1,4-cyclohexadiene, and oxocyclohexadiene, even more preferably from 1,3-cyclohexadiene, 1,4-cyclohexadiene, and oxocyclohexadiene that are each independently substituted with one or more substituents R2, each R2 being independently selected from methyl ($CH_3$), ethyl ($C_2H_5$), propyl ($C_3H_7$) and mixtures thereof. In the most preferred embodiment where A is 1, Y is either 1,3-cyclohexadiene, 1,4-cyclohexadiene, oxocyclohexadiene, 1,3-cyclohexadiene substituted with 1 to 2 R2 groups, 1,4-cyclohexadiene substituted with 1 to 2 R2 groups, and oxocyclohexadiene substituted with 1 to 2 R2 groups, each of the R2 groups of 1,3-cyclohexadiene 1,4-cyclohexadiene and oxocyclohexadiene being independently selected from methyl ($CH_3$), ethyl ($C_2H_5$) and mixtures thereof.

When Y is 1,3-cyclohexadiene, 1,4-cyclohexadiene, substituted 1,3-cyclohexadiene or substituted 1,4-cyclohexadiene as defined hereinbefore, preferably the specific dienyl ligand is selected from cyclohexadienyl, substituted cyclohexadienyl, oxocyclohexadienyl, and substituted oxocyclohexadienyl, more preferably a cyclohexadienyl ligand that is substituted with methyl groups such as, for example, 6,6-dimethylcyclohexadienyl, 2,6,6-trimethylcyclohexadienyl, or an oxocyclohexadienyl that is substituted with methyl groups, such as, for example, 6-oxo-2-methylcyclohexadienyl.

In the case where A is equal to 1 and Y is cyclohexadiene, preferably the cyclohexadiene utilized is a 1,4-cyclohexadiene. In the most preferred embodiments, the ligand 1,4-cyclohexadiene is functionalized (includes a functionalized/substituted group such as a $C_1$ to $C_4$ alkyl group), which will enable the enhancement of the properties of the precursor (for example: lower melting point).

The difference in structures between 1,3-cyclohexadiene and 1,4-cyclohexadiene is shown below. The boat configuration of 1,4-cyclohexadienyl increases the asymmetry of the molecule which is in turn beneficial to the decrease of the melting point.

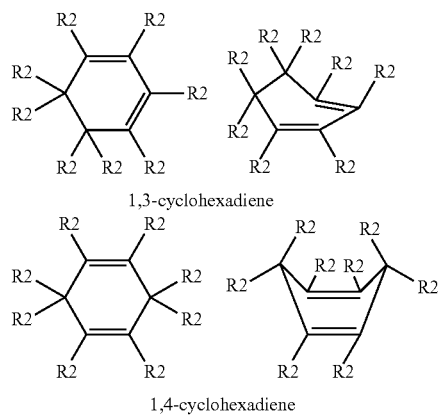

1,3-cyclohexadiene 1,4-cyclohexadiene

Another particularly preferred embodiment of the formula (I) is when A is equal to 1, X is cyclopentadienyl that is either unsubstituted or substituted with from 1 to 3 $C_1$ to $C_4$ alkyl groups and Y is an 1-methyl-1,4-cyclohexadine. With regard to these particular compounds, preferably X is a cyclopentadienyl group that is unsubstituted or is a cyclopentadienyl group that is substituted with one ethyl group.

Note that with regard to the embodiments where A is equal to one and X is cyclopentadienyl that is substituted with one functional group selected from hydrogen and $C_1$ to $C_4$ alkyl, Y cannot be either a 1,3-cyclohexadiene or butadiene optionally substituted by an unlimited number of substituents R2, wherein each R2 is hydrogen, a $C_1$ to $C_6$ alkoxy group or a $C_1$ to $C_6$ alkyl group. Even more specifically with regard to the present invention, the iridium precursor will not be methylcyclopentadienyl (1,3-cyclohexadiene) iridium or ethylcyclopentadienyl (1,3-cyclohexadiene) iridium, the 1,3-cyclohexadiene being either unsubstituted or substituted with functional group(s), ethylcyclopentadienyl butadiene iridium, the butadiene ligand being either unsubstituted or substituted.

In the second embodiment of the present invention where A is equal to 2 (there are two Y groups), X is selected from dienyl ligands and Y is selected from CO and substituted or unsubstituted ethylene ligands. In this particular embodiment, the dienyl ligand X is selected from cyclopentadienyl (Cp), pentadienyl (Op), cyclohexadienyl (chdl), hexadienyl, oxocyclohexadienyl, cycloheptadienyl, heptadienyl, cyclooctadienyl, and octadienyl. Each of the noted ligands can optionally be substituted with an unlimited number of substituents R3, with each R3 being independently selected from H, O, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides, and $C_1$ to $C_4$ linear or branched fluoroalkyl, with the proviso that when X is pentadienyl, cyclopentadienyl, or cycloheptadienyl, the X substituents can not be fully substituted; they will lack at least one substitution thereby leaving at least one available site for substitution. When the dienyl ligands are cyclopentadienyl (Cp) or cyclohexadienyl (chdl), they will preferably each be substituted with an unlimited number of substituents R3 that are selected from methyl ($CH_3$), ethyl ($C_2H_5$), propyl ($C_3H_7$) and mixtures thereof, provided that in the case of cyclopentadienyl, the substitution will not be full substitution. In the most preferred embodiments, the dienyl ligand is selected from cyclopentadienyl (Cp) and cyclohexadienyl (chdl) which is substituted with from 1 to 3 R3 substituents that are each independently selected from methyl ($CH_3$) and ethyl ($C_2H_5$), provided that as noted above when X is cyclopentadienyl, the substitution will not be full substitution.

Furthermore, in this particular embodiment where A is 2, each Y is independently selected from CO and an ethylene ligand of the formula (II):

wherein each R4, R5, R6 and R7 is independently selected from H, $C_1$ to $C_8$ linear or branched alkyl, $C_1$ to $C_8$ linear or branched haloalkyl, $C_1$ to $C_8$ linear or branched alkoxy, $C_1$ to $C_8$ linear or branched alkylamino, $C_1$ to $C_8$ linear or branched alkylsilyl, and $C_1$ to $C_8$ linear or branched alkylsilylamino. Accordingly, the general structure of the ethylene ligand will be

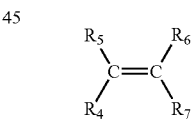

In this embodiment, particular attention is paid to the selection of each of R4, R5, R6 and R7 in order to tune the physical properties of the iridium molecules, such as thermal stability, volatility, and melting point. For example, the following case could be considered: 1-methyl, 1-ethyl-ethylene (also called 2-methyl, 1-butene), in which R4 is methyl and R5 is ethyl, while R6 and R7 are each H. With regard to this particular embodiment, when A is equal to two and X is cyclopentadienyl or cyclopentadienyl that is substituted with one functional group selected from $C_1$ to $C_6$ alkyl, each Y cannot be an ethylene ligand or an ethylene ligand that is substituted (substitution at one of R4, R5, R6 or R7), with hydrogen or $C_1$ to $C_6$ alkyl.

In addition, when A is equal to two and X is cyclopentadienyl or cyclopentadienyl that is substituted with one functional group selected from lower ($C_1$ to $C_6$) alkyl, each Y cannot be a CO ligand.

Finally, when A is equal to two and X is pentamethylcyclopentadienyl, both Y groups cannot be ethylene. More specifically, with regard to these provisos, the iridium precursor will never be cyclopentadienyl dicarbonyl iridium, with the cyclopentadienyl being substituted or unsubstituted, cyclopentadienyl bis(ethylene) iridium, with the ethylene ligand or the cyclopentadienyl ligand being substituted with one substitution group or unsubstituted.

The third embodiment of the present invention exists when A is equal to 2 (there are two Y groups) in the formula (I):

and X is a H, an alkyl, an alkylamide, an alkoxide, an alkylsilyl, an alkylsilyamide, an alkylamino or a fluoroalkyl and each Y is a diene ligand. More specifically, in this particular embodiment, X will be a ligand selected from H, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides, $C_1$ to $C_4$ linear or branched alkylamino, and $C_1$ to $C_4$ linear or branched fluoroalkyl. Of these ligands, X is preferably selected from ethyl ($C_2H_5$), propyl ($C_3H_7$) and butyl ($C_4H_9$). Furthermore, with regard to this particular embodiment, each Y is a diene ligand and is independently selected from butadiene, cyclopentadiene, pentadiene, hexadiene, 1,3-cyclohexadiene, 1,4-cyclohexadiene, and oxocyclohexadiene. Each of the diene ligands represented by Y may optionally be substituted by an unlimited number of substituents R8, with each R8 being independently selected from H, O, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides, and $C_1$ to $C_4$ linear or branched fluoroalkyl. With regard to the diene ligands represented by Y, in this particular embodiment, each Y will preferably be independently selected from butadiene ($C_4H_6$) and 1,4-cyclohexadiene ($C_6H_8$). When each Y is independently selected from butadiene ($C_4H_6$) and 1,4-cyclohexadiene ($C_6H_8$), the butadiene ($C_4H_6$) and 1,4-cyclohexadiene ($C_6H_8$) will also preferably be substituted with an unlimited number of substituents R8 that are selected from methyl ($CH_3$), ethyl ($C_2H_5$) and propyl ($C_3H_7$). In the most preferred embodiments, the diene ligands are selected from butadiene ($C_4H_6$), butadiene substituted with from 1 to 2 R8 groups with each R8 group independently selected from methyl ($CH_3$) and ethyl ($C_2H_5$), 1,4-cyclohexadiene ($C_6H_8$), and 1,4-cyclohexadiene substituted with from 1 to 2 R8 groups with each R8 group independently selected from methyl ($CH_3$) and ethyl ($C_2H_5$).

When Y is cyclohexadiene or substituted cyclohexadiene as defined hereinbefore, preferably the specific dienyl ligand is selected from cyclohexadienyl, substituted cyclohexadienyl, oxocyclohexadienyl or substituted oxocyclohexadienyl, more preferably a cyclohexadienyl ligand that is substituted such as, for example, 6,6-dimethylcyclohexadienyl, 2,6,6-trimethylcyclohexadienyl, or an oxocyclohexadienyl that is substituted, such as, for example, 6-oxo-2-methylcyclohexadienyl.

A still further preferred embodiment exists when X is a $C_1$ to $C_4$ alkyl group (preferably propyl, even more preferably iso-propyl) and Y is a cyclohexadiene or butadiene. More specifically, preferred embodiments of the iridium molecule described hereinbefore are represented by Ir(butadiene)$_2$(iso-propyl) or by Ir(cyclohexadiene)$_2$(isopropyl).

As in the previous embodiment where Y is a diene ligand, in this third embodiment, when Y is cyclohexadiene, the hexadiene is preferably 1,4-cyclohexadiene as described hereinbefore (with the exception that the R groups will be R8 groups instead of R2 groups).

The fourth and final embodiment of the present invention exists when A is equal to 2 (there are two Y groups) in the formula (I):

and X is a dienyl ligand and each Y is a diene ligand. In this particular embodiment, X is a dienyl ligand selected from cyclopentadienyl (Cp), pentadienyl (Op), cyclohexadienyl (chdl), hexadienyl, oxocyclohexadienyl, cycloheptadienyl, heptadienyl, cyclooctadienyl, and octadienyl. Each of the dienyl ligands may optionally be substituted with an unlimited number of substituents R9, each R9 being independently selected from H, O, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides, and $C_1$ to $C_4$ linear or branched fluoroalkyl.

In the present embodiment, X is preferably selected from cyclopentadienyl (Cp) and cyclohexadienyl (chdl), even more preferably cyclopentadienyl (Cp) and cyclohexadienyl (chdl) that are each independently substituted with one or more substituents R9, each R9 being independently selected from methyl ($CH_3$), ethyl ($C_2H_5$) and propyl ($C_3H_7$). Preferably in this embodiment, when A is 2, X is either substituted cyclopentadienyl (Cp) or substituted cyclohexadienyl (chdl), each being substituted with from 1 to 7 R9 groups, preferably from 1 to 5 R9 groups, with each R9 group being independently selected from methyl ($CH_3$) and ethyl ($C_2H_5$).

Y is a diene ligand selected from butadiene, cyclopentadiene, pentadiene, hexadiene, 1,3-cyclohexadiene, 1,4-cyclohexadiene, and oxocyclohexadiene. Each of these diene ligands can optionally be substituted with an unlimited number of substituents R10, each R10 being independently selected from H, O, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides, and $C_1$ to $C_4$ linear or branched fluoroalkyl. With regard to the diene ligands represented by Y, in this particular embodiment, each Y will preferably be independently selected from butadiene ($C_4H_6$), 1,3-cyclohexadiene ($C_6H_8$), and 1,4-cyclohexadiene ($C_6H_8$), oxocyclohexadiene and mixtures thereof. When each Y is independently selected from butadiene ($C_4H_6$), 1,3-cyclohexadiene ($C_6H_8$), and 1,4-cyclohexadiene ($C_6H_8$), the butadiene ($C_4H_6$), 1,3-cyclohexadiene ($C_6H_8$), and 1,4-cyclohexadiene ($C_6H_8$) will also preferably be substituted with an unlimited number of substituents R10 that are selected from methyl ($CH_3$), ethyl ($C_2H_5$), propyl ($C_3H_7$) and mixtures thereof. In the most preferred embodiments, the diene ligands are selected from butadiene ($C_4H_6$), butadiene substituted with from 1 to 2 R10 groups with each R10 group independently selected from methyl ($CH_3$) and ethyl ($C_2H_5$), and 1,4-cyclohexadiene substituted with from 1 to 2 R10 groups with each R10 group independently selected from methyl ($CH_3$) and ethyl ($C_2H_5$).

With regard to this embodiment, when X is a substituted pentadienyl, a substituted cyclopentadienyl, or a substituted cycloheptadienyl, the X substituents will not be fully substituted; they will lack at least one substitution to qualify as full substitution thereby leaving at least one available site for substitution.

When Y is cyclohexadiene or substituted cyclohexadiene as defined hereinbefore, preferably the specific dienyl ligand is selected from cyclopentadienyl, substituted cyclopentadienyl, hexadienyl, substituted hexadienyl, cyclohexadienyl, substituted cyclohexadienyl, oxocyclohexadienyl or substituted oxocyclohexadienyl, more preferably they are selected from a cyclopentadienyl ligand and a substituted cyclopentadienyl ligand, such as, for example, methylcyclopentadienyl and ethylcyclopentadienyl. Examples of the molecules described by such embodiment are, but are not limited to, ethylcyclopentadienyl bis(1-methyl-1,4-cyclohexadiene) iridium and ethylcyclopentadienyl bis(1,3-cyclohexadiene) iridium.

Based on the above noted embodiments, examples of the iridium containing precursors of the present invention can be selected from, but are not limited to:
cyclopentadienyl (1,4-cyclohexadiene) iridium,
cyclopentadienyl (1-methyl-1,4-cyclohexadiene) iridium,
ethylcyclopentadienyl (1-methyl-1,4-cyclohexadiene) iridium,
(2,6,6-trimethylcyclohexadienyl)(1-Me-1,4-cyclohexadiene) iridium,
bis(ethylene)(cyclohexadienyl) iridium,
bis(ethylene)(ethylcyclohexadienyl) iridium,
bis(1-methyl-1-ethyl-ethylene)(ethylcyclohexadienyl) iridium,
bis(1-methyl-1-ethyl-ethylene)(ethylcyclopentadienyl) iridium,
bis(1,3-cyclohexadiene) (ethylcyclopentadienyl) iridium,
bis(1,4-cyclohexadiene) (ethylcyclopentadienyl) iridium,
bis(1-methyl-1,4-cyclohexadiene) (ethylcyclopentadienyl) iridium,
bis(butadiene)$_2$(isopropyl) iridium
and mixtures of these iridium containing precursors.

With regard to the specific embodiments noted above, it is further noted that these embodiments do not include the following molecules:
(1,3-cyclohexadiene)IrCp,
(butadiene)IrCp,
(CO)$_2$IrCp,
(hexadiene)IrCp, in which the Cp ligand is substituted by one group selected from hydrogen and a $C_1$ to $C_6$ alkyl, and the diene is substituted by a number of substituents being independently selected from hydrogen, a $C_1$ to $C_6$ alkoxy group or a $C_1$ to $C_6$ alkyl group;
(ethylene)$_2$IrCp, in which the Cp ligand can be substituted by one group selected from hydrogen and $C_1$ to $C_6$ alkyl, and the ethylene ligand can be substituted by one substituent being selected from hydrogen and a $C_1$ to $C_6$ alkyl group;
and (ethylene)$_2$Ir(pentamethylcyclopentadienyl.

The next step in the process involves reacting the at least one iridium containing precursor in the reactor wherein the reactor is set at a temperature equal to or higher than 100° C. With regard to this step, preferably the temperature conditions range from about 100° C. to about 500° C. In an even more preferred embodiment, the temperature will range from about 150° C. to about 350° C. As used herein, the term "reacting" refers to the thermal decomposition or pyrolysis of the iridium molecule and also the reaction of the iridium molecule with another vapor that may be introduced simultaneously or separately with the iridium vapors.

The pressure in the reactor will preferably be between about 1 Pa and $10^5$ Pa. In the preferred embodiment, the pressure will be between about 25 Pa and about $10^3$ Pa. Note that after the substrate is added to the reactor, the reactor door is closed and the pressure is decreased to the desired level before the heating of the reactor takes place. Those of ordinary skill in the art will recognize that the pressure in the reactor may be maintained or it may be changed at least one order of magnitude during the actual reacting of the at least one iridium containing precursor. Accordingly, the process of the present invention is meant to cover both processes those which have a maintained pressure level and those which include shifts in pressure also.

The process of the present invention may further comprise the additional step of providing at least one reducing fluid in to the reactor. The at least one reducing fluid is preferably selected from the group consisting of $H_2$, $NH_3$, $SiH_4$, $Si_2H_6$, $Si_3H_8$, hydrogen containing fluids, hydrogen containing radicals, such as H. and NH., and mixtures thereof. Of the selected reducing fluids, the most preferred reducing fluids are $H_2$ and $NH_3$ and combinations thereof.

The process of the invention may still further comprise the additional step of providing at least one oxygen containing fluid in to the reactor. The at least one oxygen containing fluid is preferably selected from the group consisting of $O_2$, $O_3$, $H_2O$, $H_2O_2$, NO, $NO_2$, $N_2O$, oxygen containing radicals such as O. or OH. and mixtures thereof. Of the selected oxygen containing fluids, the most preferred oxygen containing fluids are $O_2$, $O_3$ and $H_2O$ and combinations thereof.

Note that the manner in which the hydrogen containing fluid and the oxygen containing fluid are introduced into the reactor may vary depending upon the type of deposition that is being used (for example, CVD or ALD). Accordingly, these various reactants (the reducing fluids and/or the oxygen containing fluids) can be introduced into the reactor either simultaneously (at the same time; for example by chemical vapor deposition), sequentially (one after the other; for example by atomic layer deposition) or different combinations thereof. Another example is when using a hydrogen-containing fluid, to introduce the hydrogen-containing fluid and/or the oxygen-containing fluid continuously and to introduce the at least one metal source by pulse (for example, by pulsed chemical vapor deposition).

The above defined iridium containing precursors introduced into the reactor in the second step of the current process are typically liquids. In other words, they preferably have a melting point below about 25° C. Even more preferably, the iridium containing precursors will have a melting point at or below about 0° C.

The present invention further relates to a specific iridium containing precursor of the formula (I):

$$XIrY_A \qquad (I)$$

wherein A is equal to 1, X is cyclopentadienyl that is substituted with from 1 to 3 $C_1$ to $C_4$ alkyl groups and Y is 1-methyl-1,4-cyclohexadiene. With regard to these particular compounds, in the preferred embodiment, X is a cyclopentadienyl group with is substituted with one ethyl group. Note that this compound has the benefit that it is more volatile and more reactive.

For the purpose of example only, the molecules (2,6,6-trimethylcyclohexadienyl)(1-Me-1,4-cyclohexadiene) iridium, (ethylcyclopentadienyl)(1-Methyl-1,4-cyclohexadiene) iridium, and bis(1,3-butadiene)(isopropyl) iridium are represented below in order to show the type of metal containing precursors contemplated for use in the process of the present invention.

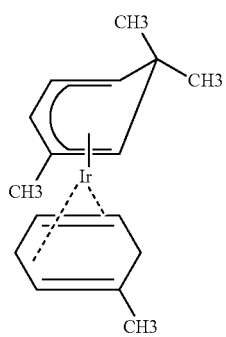

(2,6,6-trimethylcyclohexadienyl)
(1-Me-1,4-cyclohexadiene) iridium

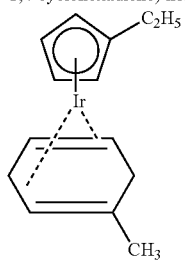

(ethylcyclopentadienyl)
(1-Methyl-1,4-cyclohexadiene) iridium

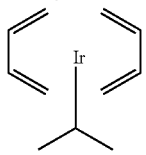

bis(1,3-butadiene)(isopropyl) iridium

According to another embodiment of the present invention, the metal containing film deposited on to the substrate shall be a metallic film, a metal oxide film, or an alloy with another metallic element such as for example, platinum.

Examples of the present invention will now be disclosed along with reference to the chemical structures of the various examples. The examples included herein are provided by way of example alone and are in now way intended to limit the scope of the present invention.

EXAMPLES

Example 1

Proposed Synthesis of (1,4-cyclohexadiene)(2,6,6-trimethylcyclohexadienyl) iridium Chlorobis(1,4-cyclohexadiene)iridium can be synthesized utilizing the procedure set forth in by G. Winkhaus and H. Singer, Chem. Ber., 99, 3610 (1966). More specifically, Iridium chloride and 1,4-cyclohexadiene is to be added to ethanol and water, and the mixture allowed to react for 1 day under refluxing conditions. After cooling, the deposit obtained is to be filtered and then dried to obtain chlorobis(1,4-cyclohexadiene)iridium. This product is then to be added to tetrahydrofuran (THF). A reaction flask is then cooled to −78° C. and the THF solution of 2,6,6-trimethyl-cyclohexadiene added. (As an alternative, Zn dust can also be added). The resulting mixture is then to be stirred at −78° C. for several minutes, and the temperature then raised to around 25° C. (room temperature) in a stepwise fashion. The resulting mixture is then to be allowed to further react for several hours. The mixture obtained is then to be concentrated until an orange mixture is obtained. This mixture can be extracted using hexane, and the resulting solution subjected to column chromatography to obtain the desired product of (1,4-cyclohexadiene)(2,6,6-trimethylcyclohexadienyl) iridium.

Example 2

Proposed Deposition of Iridium and Iridium Containing Films

Iridium precursors according to the present invention allow for their further use without the addition of a solvent.
Proposed Deposition of Pure Iridium Films
Pure iridium films can be deposited at temperatures above 200° C. The liquid precursor is stored in a bubbler kept at a temperature of 60° C. and delivered to a hot-wall reactor by a bubbling method. An inert gas, helium in most cases, can be used as a carrier gas, as well as for dilution purpose. Tests can be done with oxygen as co-reactant in CVD mode. The composition of the films can be checked by various techniques (Auger, RBS) to confirm that pure iridium films are obtained.
Proposed Atomic Layer Deposition
The iridium precursors are suitable for the atomic layer deposition (ALD) of iridium films at low temperatures (150° C. to 350° C.) using the appropriate co-reactant. Metallic iridium depositions in ALD technique are possible when the co-reactant is molecular and atomic oxygen, as well as with other oxidants.
Proposed Deposition of Iridium-Platinum Films
Iridium-platinum films can be deposited by making the iridium precursor and a platinum precursor, such as (MeCp)PtMe$_3$, react in a deposition furnace with an oxygen containing fluid. In this particular case, the oxygen containing fluid is preferably oxygen. Iridium-platinum depositions in CVD and ALD technique are possible. The ratio or Ir/Pt can be adjusted according to the needs by increasing or decreasing the flow of precursor of each metallic precursor.

What is claimed is:
1. A process for the deposition of a iridium containing film on a substrate, the process comprising the steps of:
A) providing at least one substrate in a reactor;
B) introducing into the reactor at least one iridium containing precursor having the formula:

$XIrY_A$, i) when A is 1,
(a) X is a dienyl ligand selected from 6,6-dimethylcyclohexadienyl, 2,6,6-trimethylcyclohexadienyl, or 6-oxo-2-methylcyclohexadienyl;
Y is a diene ligand selected from butadiene, cyclopentadiene, pentadiene, hexadiene, 1,3-cyclohexadiene, 1,4-cyclohexadiene, and oxocyclohexadiene, each diene ligand optionally substituted with one or more substituents R2, each R2 being independently selected from H, O, $C_1$ to $C_4$ linear or branched alkyl, $C_1$ to $C_4$ linear or branched alkylamides, $C_1$ to $C_4$ linear or branched alkoxides, $C_1$ to $C_4$ linear or branched alkylsilyls, $C_1$ to $C_4$ linear or branched alkylsilylamides, and $C_1$ to $C_4$ linear or branched fluoroalkyl; or
(b) X is a cyclopentadienyl (Cp) substituted with 1 to 3 $C_1$ to $C_4$ alkyl groups;
Y is a substituted 1,4-cyclohexadiene;

C) reacting the at least one iridium containing precursor in the reactor at a temperature equal to or greater than 100° C.; and D) depositing an iridium containing film formed from the reaction of the at least one iridium containing precursor onto the at least one substrate.

2. The process of claim 1, wherein step c) takes place at a temperature range from 100° C. to 500° C.

3. The process of claim 1, wherein step c) takes place at a temperature range from 150° C. to 350° C.

4. The process of claim 2, wherein the pressure in the reactor is between 1 Pa and $10^5$ Pa.

5. The process of claim 3, wherein the pressure in the reactor is between 25 Pa and $10^3$ Pa.

6. The process of claim 1, wherein the process further comprises the additional step of introducing at least one reducing fluid into the reactor, the reducing fluid being selected from the group consisting of $H_2$, $NH_3$, $SiH_4$, $Si_2H_6$, $Si_3H_8$, hydrogen containing fluids, hydrogen radicals and mixtures thereof.

7. The process of claim 6, wherein the process further comprises the additional step of introducing at least one oxygen containing fluid into the reactor, the oxygen containing fluid selected from the group consisting of $O_2$, $O_3$, $H_2O$, $H_2O_2$, NO, $NO_2$, $N_2O$, oxygen containing radicals such as O. or OH. and mixtures thereof.

8. The process of claim 1, wherein the process further comprises the additional step of introducing at least one oxygen containing fluid into the reactor, the oxygen containing fluid selected from the group consisting of $O_2$, $O_3$, $H_2O$, $H_2O_2$, NO, $NO_2$, $N_2O$, oxygen containing radicals such as O. or OH. and mixtures thereof.

9. The process of claim 1, wherein the process further comprises the additional step of introducing at least one fluid containing vapors of another metallic precursor in combination with
a) at least one reducing fluid selected from the group consisting of $H_2$, $NH_3$, $SiH_4$, $Si_2H_6$, $Si_3H_8$, hydrogen containing fluids, hydrogen radicals and mixtures thereof; or
b) at least one oxygen containing fluid selected from the group consisting of $O_2$, $O_3$, $H_2O$, $H_2O_2$, NO, $NO_2$, $N_2O$, oxygen containing radicals such as O. or OH. and mixtures thereof; or
c) at least one reducing fluid selected from the group consisting of $H_2$, $NH_3$, $SiH_4$, $Si_2H_6$, $Si_3H_8$, hydrogen containing fluids, hydrogen radicals and mixtures thereof and at least one oxygen containing fluid selected from the group consisting of $O_2$, $O_3$, $H_2O$, $H_2O_2$, NO, $NO_2$, $N_2O$, oxygen containing radicals such as O. or OH. and mixtures thereof.

10. The process of claim 9, wherein the other metallic precursor is a platinum precursor.

11. The process of claim 1, wherein the iridium containing film is deposited on a substrate by chemical vapor deposition (CVD), atomic layer deposition (ALD), pulse-CVD, or other known techniques of deposition.

12. An iridium containing precursor of the formula (I):

$$XIrY_A \qquad (I)$$

wherein A is equal to 1, X is 1,4-cyclopentadienyl that is substituted with from 1 to 3 $C_1$ to $C_4$ alkyl groups and Y is 1-methyl-1,4-cyclohexadiene.

13. The iridium containing precursor of claim 12, wherein the 1,4-cyclopentadienyl is substituted with one ethyl group.

* * * * *